United States Patent
Edvardsen

(10) Patent No.: US 6,877,565 B2
(45) Date of Patent: Apr. 12, 2005

(54) ARRANGEMENT FOR THE REMOVAL OF CUTTINGS AND GAS ARISING FROM DRILLING OPERATIONS

(75) Inventor: Per Espen Edvardsen, Loddefjord (NO)

(73) Assignee: AGR Services AS, Straume (NO)

( * ) Notice: Subject to any disclaimer, the term of this patent is extended or adjusted under 35 U.S.C. 154(b) by 47 days.

(21) Appl. No.: 10/334,333

(22) Filed: Dec. 26, 2002

(65) Prior Publication Data

US 2003/0132028 A1 Jul. 17, 2003

Related U.S. Application Data

(63) Continuation-in-part of application No. 09/700,960, filed as application No. PCT/NO99/00165 on May 25, 1999, now abandoned.

(30) Foreign Application Priority Data

| Apr. 13, 2000 | (NO) | 2000 1920 |
| Jul. 13, 2000 | (NO) | 2000 3591 |
| Apr. 10, 2001 | (WO) | PCT/NO01/00160 |
| Jul. 13, 2001 | (WO) | PCT/NO01/00301 |

(51) Int. Cl.$^7$ ............................................. E21B 49/00
(52) U.S. Cl. ........................... 166/352; 166/84.1; 175/7
(58) Field of Search ................................. 166/352, 358, 166/360, 84.1; 175/5, 7

(56) References Cited

U.S. PATENT DOCUMENTS

| 4,326,584 A | * | 4/1982 | Watkins ..................... 166/84.2 |
| 4,444,250 A | * | 4/1984 | Keithahn et al. .......... 166/84.4 |
| 4,456,063 A | * | 6/1984 | Roche ........................ 166/84.4 |
| 5,010,966 A | * | 4/1991 | Stokley et al. ................ 175/66 |
| 2003/0182997 A1 | * | 10/2003 | Williams ................. 73/152.23 |

* cited by examiner

*Primary Examiner*—William Neuder
(74) *Attorney, Agent, or Firm*—Francis C. Hand; Carella, Byrne, Bain et al.

(57) ABSTRACT

An end piece arrangement is mounted on an end of a pipe sleeve to close off the annular passage between the pipe sleeve and drill stem and to divert an upward flow of sludge, cuttings and gas into a conduit system to transport the flow to a remote location. In one embodiemnt, the arrangement is a self-contained unit that houses seal rings to seal against the drill stem. In another embodiment, the arrangement includes separate components; i.e. a housing mounted on the pipe sleeve to divert the upward flow and a seal unit mounted on the drill stem and rotatably mounted in the housing.

21 Claims, 4 Drawing Sheets

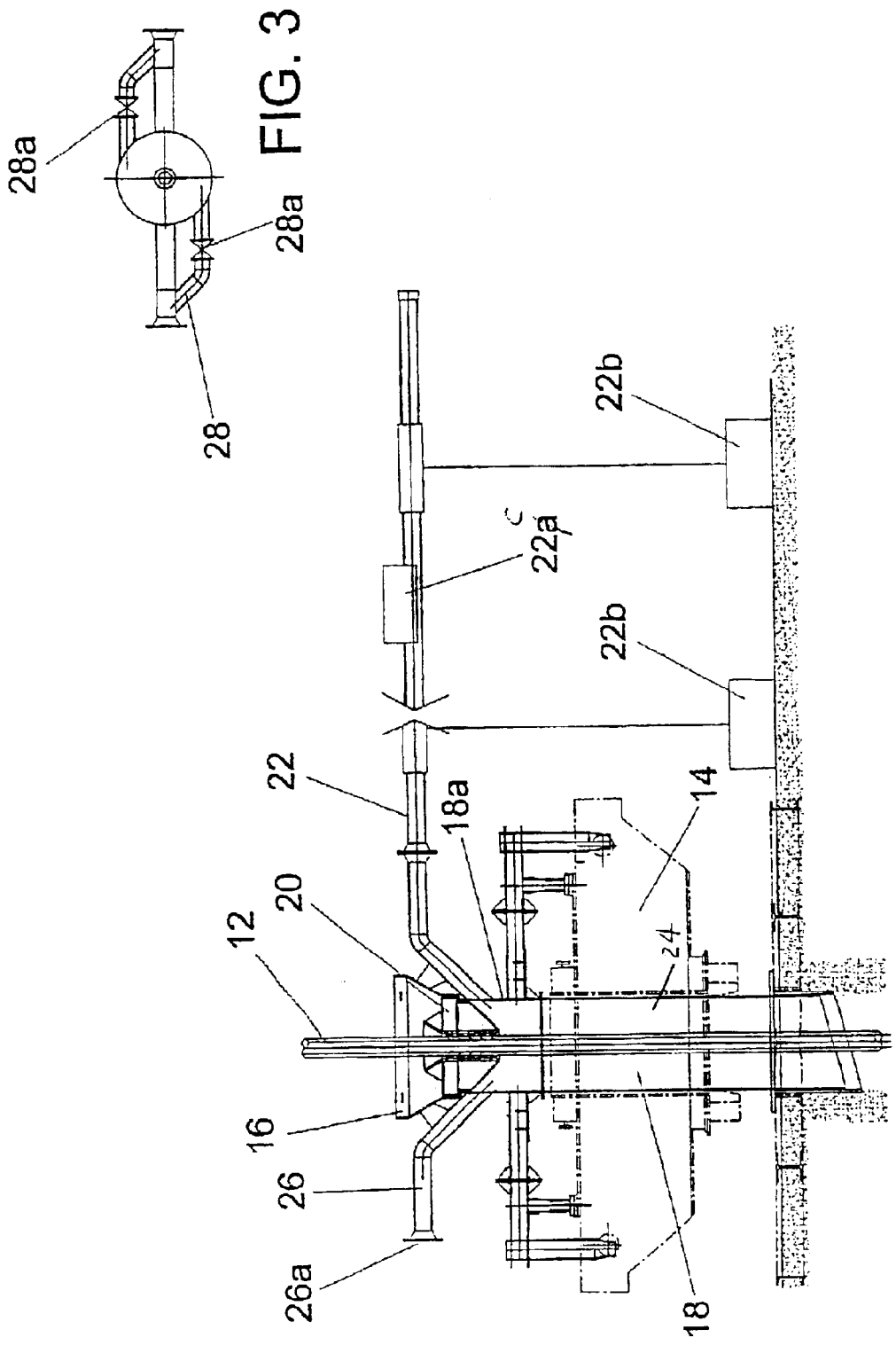

ARRANGEMENT FOR THE REMOVAL OF CUTTINGS AND GAS ARISING FROM DRILLING OPERATIONS

This application is a Continuation-in-Part of Ser. No. 09/700,960, filed Nov. 22, 2000 now abandoned, which is the national stage of International App. No. PCT/NO99/00165 filed on May 25, 1999.

This invention relates to an arrangement for the removal of cuttings and gas arising from drilling operations. More particularly, this invention relates to an arrangement for the removal of cuttings, mud, clay, gas and the like in connection with top hole boring in wells As is known, during top hole boring with floating rigs, gas represents a problem in the first phases of drilling when the sleeve pipes have not been set. With large quantities of gas, the drilling must be terminated in order to avoid sinking of the rig because of reduced buoyancy.

When drilling on the ocean bottom, it is common to employ remotely controlled underwater vehicles (ROV— remote operated vehicle) with cameras for monitoring and performance operations. However, the bore cuttings/dust that form around the boring gauge (template) during drilling, particularly in the region around the mouth of the bore hole, represent a significant visibility problem. Bore cuttings are fragments of species of stone that are brought up with the drill sludge during drilling.

Norwegian Patent NO 302043 describes a submersible ejector-driven dredging apparatus which operates on the sea bottom to transfer bore cuttings via a hose from the mouth of the bore hole to another location on the bottom of the sea. This dredging apparatus is hoisted down from a drilling rig and is thus connected to the rig by both wire and electric cables.

The problem with accumulations of bore cuttings at the mouth of the bore hole is solved by the present invention in a simpler manner by employing rig pumps on the drilling rig to expel the bore cuttings to a conduit system. In order to make this possible, an end piece arrangement is mounted between the drilling stem and the sleeve pipe and is constructed to ensure a fluid-tight seal between the sleeve pipe and the drill stem. The end piece is provided in that portion which faces towards the drill stem with elastic sealing means, for example rondelles. In addition, at least one exit passage is arranged in the sleeve pipe, which is directly, connected with a conduit system which guides the bore cuttings and the like to a location which is at a distance from the mouth of the bore hole.

In one embodiment, the end piece arrangement is mounted on an end of the sleeve pipe for sealing the annular space and at least one exit passage is formed in the sleeve pipe adjacent the end piece for passage of a flow of bore cuttings, gas and bore sludge from the annular space to a conduit system for removal to a remote site. In this embodiment, the end piece arrangement contains seals for sealing against the drill stem while allowing for relative rotation between the seals and the drill stem.

In another embodiment, the end piece arrangement is constructed of separate components for separately mounting on the pipe sleeve and the drill stem with the seals mounted in stationary relation to the drill stem.

The invention will now be further explained with reference to the accompanying drawings wherein:

FIG. 2 shows an end piece positioned between a sleeve pipe and drill stem relative to a template and base unit and a conduit system which guides the bore cuttings away from the mouth of the bore hole in accordance with the invention;

FIG. 3 is a section of the upper portions of the installation seen from above, and illustrates a jet line built into the installation;

Figure 1:
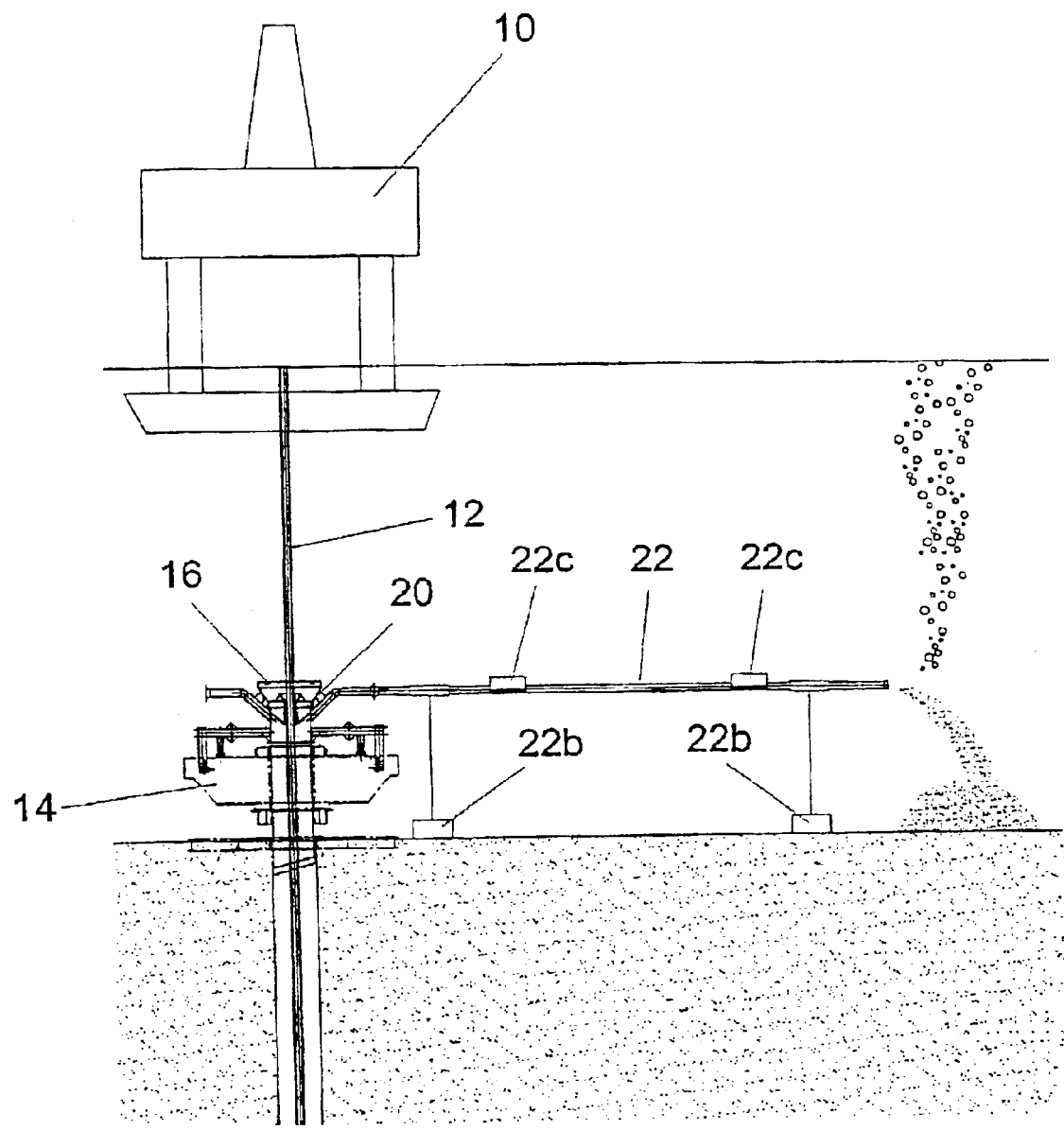
FIG. 1 shows in a general view a drilling rig (which is heavily diminished relative to the remainder of the installation), and an arrangement according to the present invention for the removal of bore cuttings.

A floating drilling rig 10 is shown in FIG. 1 in a position above the ocean bottom. From the drilling rig 10, there extends a drill stem 12 to the ocean bottom. To the ocean bottom, there is fastened a template (drilling gauge) 14. To the template 14, there is fastened a base unit 16 and a sleeve pipe 18. The drill stem 12 with associated drill crown (not shown) is guided through the sleeve pipe 18, centrally in the latter, for boring of the well.

Further FIG. 1 shows an end piece arrangement 20 and a conduit system 22 which guide bore cuttings and consumed bore sludge to a location at a distance from the mouth of the bore hole. The end piece arrangement 20 also functions as a controlling and centering arrangement for correctly positioning the drill stem 12 relative to the sleeve pipe 18, template 14 and base unit 16, at the same time as the end piece arrangement 20 ensures a substantially fluid-tight seal between the drill stem 12 and the sleeve pipe 18.

Since a substantially fluid-tight seal is thus ensured between the sleeve pipe 18 and the drill stem 12, the pressure which is established by the supply of bore sludge, by means of the rig pumps to the bore hole, that is to say the pressure increase which is formed in the annular space 24 between the sleeve pipe 18 and the drill stem 12, causes the bore cuttings, gas and consumed bore sludge to be led out through the conduit system 22. As illustrated, the conduit system is a leveled effluent system, so that the bore cuttings are led away from the mouth of the bore hole. Thus, the rig pumps are employed for removing bore sludge from the mouth of the bore hole. As a result, equipment, which is already present on drilling platforms 10, can be used to perform this task. The novel arrangement for removing bore cuttings in accordance with the invention thus has clear advantages relative to the known technique in that only two components, that is to say the end piece arrangement 20 and the conduit system 22, are to be mounted in the installation.

FIG. 2 shows in somewhat more detail how the end piece arrangement 20 is positioned between the sleeve pipe 18 and the drill stem 12. Since the drill crown has a diameter, which is greater than the drill stem 12, a longitudinal annular space 24 is formed between the inner surface of the sleeve pipe 18 and the outer surface of the drill stem 12. On drilling, bore sludge is led via the drill stem 12 down to the bore hole. Bore sludge is a liquid which is employed for a series of different functions, inter alia for maintaining control over the pressure in the well and for cooling and lubricating the drill crown. Bore sludge consists, as a rule of water, clay soil and chemicals. With a constant supply of bore sludge to the bore hole, the pressure which is established (by the rig pumps) will lead to bore cuttings, which are formed during drilling, and consumed bore sludge and gas being led via the annular space 24 up towards the surface of the ocean bottom (see FIG. 1). In known solutions, this waste will be guided between the sleeve pipe 18 and the drill stem 12 to above the upper end edge of the sleeve pipe 18. The solution according to the present invention bases itself on forming a seal between the sleeve pipe 18 and the drill stem 12, and further that there be established an exit passage in the pipe wall 18a of the sleeve pipe 18 so that the bore cuttings and sludge and possible gases are led via this opening 18a out into the conduit system 22. Bore sludge and cuttings and gas are thus led away from the mouth of the bore hole, and no longer represent a problem.

Figure 4:
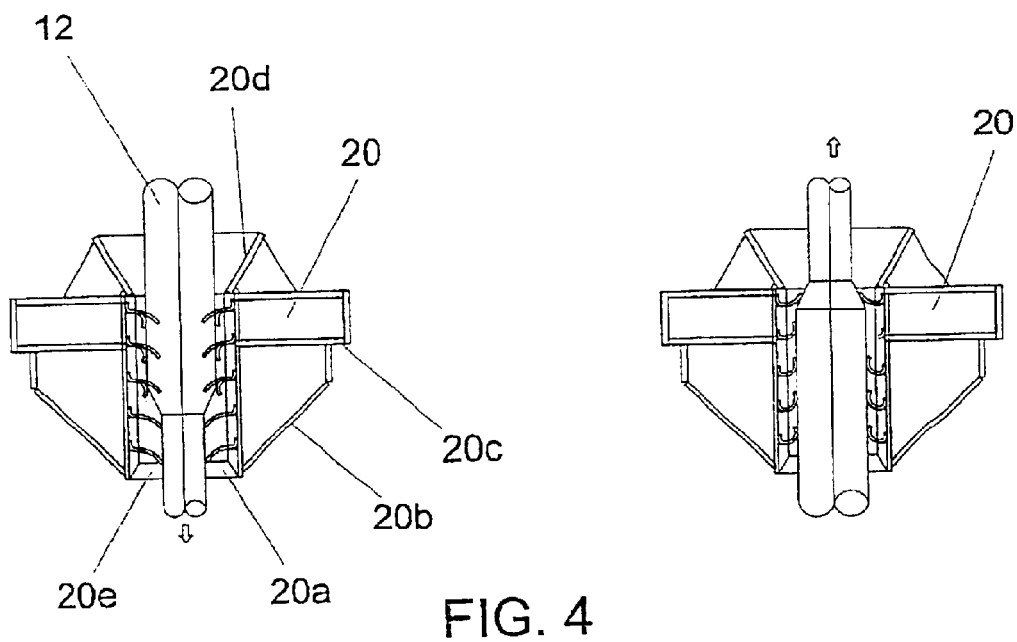
FIG. 4 shows an end piece according to the invention, and particularly how the sealing functions on feeding of the drill stem downwards ("stripping in") and upwards ("stripping out") respectively.

It is evident from FIGS. 2 and 4 how a construction of the end piece arrangement 20 is designed. The end piece arrangement 20 has an outer circular form having a diameter which is somewhat less than the inner diameter of the sleeve pipe 18 it is to be employed together with. The outer surface of the end piece arrangement 20 can be provided with sealing means, such as rubber gaskets and the like. The end piece arrangement 20 has an opening 20a in the center which is adapted to the drill stem 12 and associated sleeves 12a which it is to be employed together with, that is to say that the diameter of the opening 20a is somewhat larger than the outer diameter of the sleeve of the drill stem 12. The inner surface of the opening 20a is provided with sealing means 20e which ensure a substantially fluid-tight seal between the sleeve pipe 18 and the drill stem 12. The flexibility/elasticity of the sealing means 20e is sufficient for the seal to become substantially fluid-tight both when the drill stem 12 is enclosed by the end piece arrangement 20 and when the joint sleeves 12a are enclosed by the end piece arrangement 20.

In its lower portion, the illustrated construction of the end piece arrangement 20 is further conically designed in that these surfaces function as guide surfaces 20b for guiding the end piece arrangement 20 into place in the sleeve pipe 18. The end piece arrangement 20 also has a portion 20c with a somewhat larger periphery than the remainder of the end piece arrangement 20 in that this functions as a stop face against the upper end edge of the sleeve pipe 18. Further, in its upper portion, the end piece arrangement 20 guide surfaces 20d in connection with the penetration of the drill stem 12 in the end piece arrangement 20. By virtue of the design of the end piece arrangement 20 this will, in addition to sealing between the sleeve pipe 18 and the drill stem 12, also ensure a favorable guiding and centering of the drill stem 12 relative to sleeve pipe 18, base unit 16, template 14 and bore hole.

The opening 18a is arranged in the sleeve pipe 18 for expelling bore cuttings, sludge and gas to the conduit system 22. Preferably, this opening 18a is placed so that a flow of bore cuttings, gas and bore sludge is guided via the conical surface 20b of the end piece arrangement 20 (see FIG. 4) directly into the conduit system 22. That is to say, the opening 18a adjoins the surface 20b, i.e. surface 20b is contiguous to the opening 18a, and the angle relative to the sleeve pipe 18 on the first portion of the conduit system 22 corresponds to the angle of the conical surface 20b. As shown in FIG. 1, the conical surface 20b is continuous with the upper cylindrical surface of the conduit system 22.

FIGS. 1 and 2, show the conduit system 22 for transferring the bore cuttings, sludge and gas. The conduit system 22 is leveled in that it is equipped with anchoring elements 22b and floating elements 22c so that the major portion of the conduit system has a substantially horizontal disposition. The length of the conduit system 22 is adapted for the purpose, and is often of an order of magnitude of from 100 to 300 meters.

Since the arrangement according to the invention has a substantially fluid-tight connection for removing bore cuttings and the like, the gas will also follow with the result that the gas effluent is guided as required 100 to 300 meters from the rig and, thus, does not represent a problem.

The arrangement also includes a "back up" line 26, which can be opened with a valve 26a if the conduit system 22 is sealed shut. Further, there is in the arrangement, a jet line 28 (see FIG. 3) which makes it possible to supply via valves 28a a fluid of high pressure for detaching bore cuttings and sludge which has been stuck in the system.

FIG. 4 shows an embodiment of the sealing means 20e where these are designed as a number of rondelles 20e which extend axially from the inner surface of the end piece arrangement 20 towards the center of the opening 20a of the end piece arrangement 20. The rondelles 20e are preferably constructed of nitrile rubber since this is both elastic and wear resistant. However, other materials can be employed. The rondelles 20e can be less rigid in that portion which is in contact with the drill stem 12 than in that portion which is fastened to the end piece arrangement 20, for example, by having the thickness of the rondelles 20e decreasing towards the center. The rondelles 20e have a size and design which ensures a substantially fluid-tight coupling between the end piece arrangement 20 and drill stem 12 even if the diameter of the drill stem 12 varies.

Figure 5:
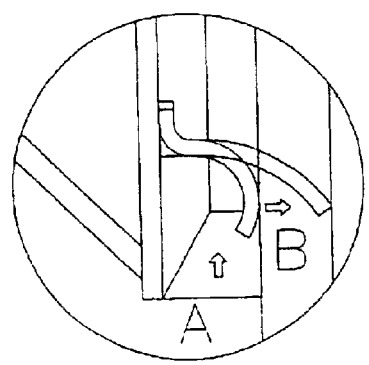
FIG. 5 shows a simplified view of how the pressure from the well ensures a fluid-tight seal between the sleeve pipe and the drill stem.

FIG. 5 illustrates in a section a rondelle 20e in contact with a drill stem 12. By virtue of the drill stem 12 being guided downwards relative to the end piece arrangement 20, the cross-section of the rondelle 20e will produce an S-shaped form. On guiding of the drill stem 12 in the opposite direction, the outer portion of the rondelle 20e is inverted and the rondelles 20e take on a U-shaped cross-sectional form.

Figure 6:
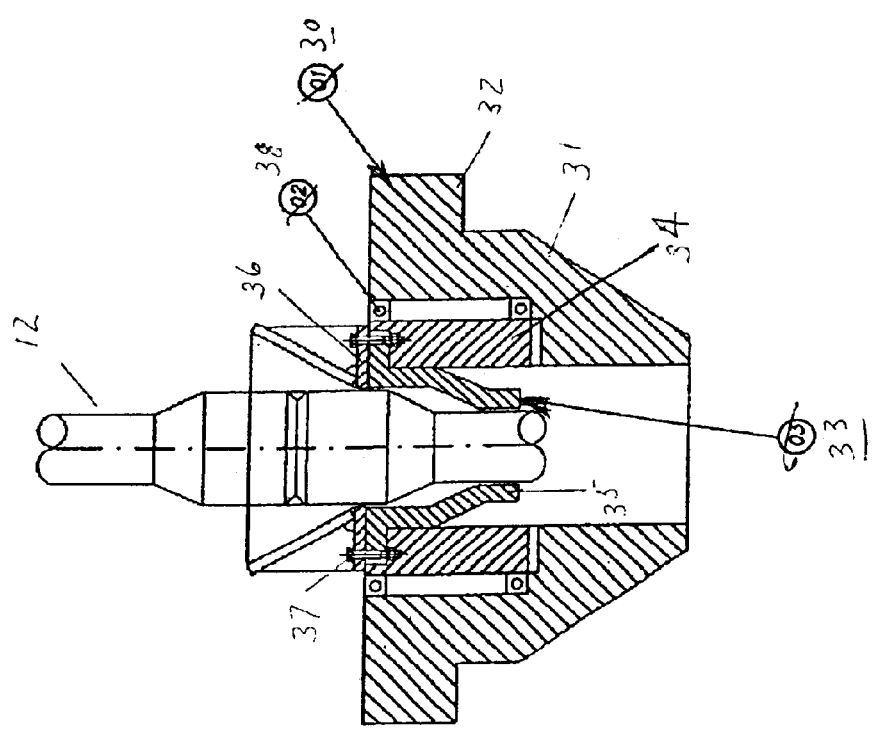
FIG. 6 illustrates a cross-sectional view of a modified end piece arrangement in accordance with the invention.

Referring to FIG. 6, wherein like reference characters indicate like parts as above, in another embodiment, an end piece arrangement includes a solid housing 30 provided with a reduced section 31 for fitting into a sleeve pipe (not shown) and cylindrical peripheral portion 32 for seating on the end of the pipe sleeve in sealed relation. The reduced section 31 also has a conical peripheral portion extending downwardly from the cylindrical portion for guiding an upward flow of material laterally thereof, and a centrally disposed opening for passage of the drill stem 12 therethrough.

In addition, the end piece arrangement has a separate seal unit 33 that is assembled and fitted on the drill stem 12. As shown, the seal unit 33 includes a sleeve 34 with an annular recess at one end, a seal ring 35 having a collar disposed in the recess of the sleeve, an annular plate 36 laid over the collar of the seal and a plurality of bolts 37 or the like securing the plate 36 to the sleeve 34 in order to hold the seal 35 in place. Suitable bearings 38 are also disposed between the sleeve 34 and the housing 30 to allow the seal unit 33 to rotate with the drill stem 12 relative to the housing 30.

The seal ring 35 serves to seal off the annular space between the drill stem 12 and the pipe sleeve (not shown) as above. In addition, the conical exterior wall of the housing 30 serves to direct a flow of sludge, cuttings and gas, as above, through an opening in the pipe sleeve into the conduit system (not shown).

This embodiment is particularly applicable to tophole/low pressure application, i.e. prior to installation of a riser and is constructed to be integrated with a sub-sea spud-base or template. In this case, the housing 30 acts as a suction and centralising module (SCM) and is installed separately on guide posts while the seal unit 33 acts as a centralisation and running tool (CRT) and is assembled on the drill stem 12 above the bottom hole assembly (BHA) on the surface (drill floor). When the drill is being run into the hole, the CRT will be guided into the SCM to form a closure. Hence, the CRT and SCM may also be used prior to casing the hole.

The seal 35 is particularly arranged for this type of use. That is the inside diameter (ID) of the seal 35 is typically 5 to 7 inches while the drill bit is typically 26 or 36 inches in diameter. Thus, the seal 35 has to be located above the BHA but not the entire arrangement.

The complete SCM/CRT guides and centers the drill stem 12 to achieve a straighter hole thereby easing conductor installation and cementing. In addition, the SCM/CRT forms an enclosed arrangement suitable for top holes, typically 36 inch and 26 inch holes, to collect the mud and cuttings from a well while diverting the flow of mud and cuttings on the seabed or pumped to the rig.

The inventive concept of the present invention is therefore that there is established a seal between the drill stem 12 and sleeve pipe 18, and that there is established an exit passage 18a for exporting bore sludge, cuttings, and gases via the opening 18a to a conduit system 22. In the same manner, the rig pumps of the drilling rig 10 can be employed to establish the force which is necessary for transferring the bore cuttings to a location at a given distance from the mouth of the bore hole.

The sleeve pipe 18 can be arranged at an angle to obtain more hydrodynamic flow conditions and the seal 20e,35 acts simply as a seal. In this respect, the seal ID may be typically 5 to 6 inches while the drill bit is typically 36 inches. Therefore, the seal has to be located above the BHA but only the seal, not the entire arrangement.

The invention further prevents the accumulation of bore cuttings and the like around the mouth of the bore hole.

The arrangement will also function as a "diverter", that is to say a diversion system for gas.

The invention is particularly useful for top hole/low pressure application, i.e. prior to installation of a riser/BOP, and is particularly useful for integration with a subsea spud-base or template. Thus, the invention may be used for first drilling a well, i.e. prior to the installation of a conductor and casing.

The SCM and CRT combination serves several purposes, e.g. guiding and centralizing the drill to obtain a straighter hole thereby easing conductor installation and cementing; and forming an enclosed arrangement suitable for top holes, typically 26 to 36 inch holes, to collect the mud and cuttings from the well while diverting the flow onto the seabed or pumping the flow to the rig.

What is claimed is:

1. An end piece arrangement for sealing an annular space between a sleeve pipe and a drill stem, said end piece arrangement comprising
    a cylindrical peripheral portion for seating on an end of the sleeve pipe,
    a conical peripheral portion extending downwardly from said cylindrical portion for guiding an upward flow of material laterally thereof,
    a centrally disposed opening for passage of a drill stem therethrough;
    a housing having said cylindrical peripheral portion, said conical peripheral portion and said opening therein; and
    a seal unit rotatably received in said housing, said seal unit including a seal ring for sealingly contacting a drill stem passing through said opening.

2. An end piece arrangement as set forth in claim 1 which further comprises sealing means mounted internally of said opening for sealing against a drill stem passing though said opening.

3. An end piece arrangement as set forth in claim 2 wherein said sealing means includes a plurality of axially spaced apart elastic rings in said opening.

4. In combination,
    a drill stem for drilling into an ocean bottom;
    a sleeve pipe disposed about said drill stem in spaced relation to define an annular space therebetween for an upward flow of bore cuttings, gas and bore sludge;
    an end piece arrangement mounted on an end of said sleeve pipe for sealing said annular space;
    at least one exit passage in said sleeve pipe adjacent said end piece for passage of a flow of bore cuttings, gas and bore sludge from said annular space to a conduit system for removal to a remote site;
    sealing means mounted internally of said end piece arrangement for sealing against said drill stem, said sealing means including a plurality of axially spaced apart elastic rings wherein each said ring has an opening smaller than said drill stem to allow flexing of said ring in a direction of axial movement of said drill stem relative to said sleeve pipe.

5. The combination as set forth in claim 4 wherein said end piece arrangement has a conical lower portion for guiding the flow of bore cuttings, gas and bore sludge from said annular space into said exit passage.

6. The combination as set forth in claim 5 further comprising a conduit system having a first portion connected to said exit passage of said sleeve pipe at an angle corresponding to the angle of said conical lower portion of said end piece arrangement.

7. The combination as set forth in claim 4 wherein said end piece arrangement has a centrally disposed opening for passage of said drill stem therethrough and a conical entry for guiding said drill stem into opening.

8. The combination as set forth in claim 4 wherein said end piece arrangement has an enlarged peripheral portion for seating against said drill stem.

9. The combination as set forth in claim 4 further comprising sealing means mounted internally of said end piece arrangement for sealing against said drill stem.

10. The combination as set forth in claim 9 wherein said sealing means is elastic to adapt to variable outer diameters of said drill stem.

11. The combination as set forth in claim 9 wherein said sealing means includes a plurality of axially spaced apart elastic rings.

12. The combination as set forth in claim 4 wherein each said ring takes on an S-shape in response to a downward movement of said drill stem and a U-shape in response to an upward movement of said drill stem relative to said sleeve pipe.

13. An arrangement for removing bore cuttings from an ocean floor, said arrangement comprising
    a drill rig;
    a sleeve pipe for embedding in the ocean floor;
    a drill stem extending from said rig and passing through said sleeve pipe into an ocean floor, said drill stem being spaced from said sleeve pipe to define an annular space therebetween;
    an end piece arrangement mounted on an end of said sleeve pipe and disposed in sealing relation with said drill stem for sealing said annular space;
    al least one exit passage in said sleeve pipe adjacent said end piece for passage of a flow of bore cuttings from said annular space;
    a conduit system in communication with and extending from said exit passage for removal of the bore cuttings to a remote site;

a plurality of axially spaced apart elastic rings mounted internally of said end piece for sealing against said drill stem wherein each said ring has an opening of smaller diameter than said drill stem to allow flexing of said ring in a direction of axial movement of said drill stem relative to said sleeve pipe.

14. The arrangement as set forth in claim 13 wherein said end piece arrangement has a conical lower portion for guiding the flow of bare cuttings from said annular space into said exit passage.

15. The arrangement a set forth in claim 14 wherein said conduit system has a first portion connected to said sleeve pipe at an angle corresponding to the angle of said conical lower portion of said end piece.

16. The arrangement as set forth in claim 13 wherein each said ring takes on an S-shape in response to a downward movement of said drill stem and a U-shape in response to an upward movement of said drill stem relative to said sleeve pipe.

17. In combination,
   a drill stem for drilling into an ocean bottom;
   a sleeve pipe disposed about said drill stem in spaced relation to define an annular space therebetween for an upward flow of bore cuttings, gas and bore sludge;
   an end piece arrangement mounted on an end of said sleeve pipe for sealing said annular space, said end piece arrangement including a housing mounted on said sleeve pipe and a seal unit mounted on said drill stem and rotatably received in said housing; and
   at least one exit passage in said sleeve pipe adjacent said end piece for passage of a flow of bore cuttings, gas and bore sludge from said annular space to a conduit system for removal to a remote site.

18. The combination as set forth in claim 17 wherein said housing has a conical lower portion for guiding the flow of bore cuttings, gas and bore sludge from said annular space into said exit passage.

19. The combination as set forth in claim 18 further comprising a conduit system having a first portion connected to said exit passage of said sleeve pipe at an angle corresponding to the angle of said conical lower portion of said housing.

20. The combination as set forth in claim 17 wherein said seal unit includes a seal ring disposed in stationary sealing contact with said drill stem.

21. An arrangement for removing bore cuttings from an ocean floor, said arrangement comprising
   a drilling rig;
   a sleeve pipe for embedding in the ocean floor;
   a drill stem extending from said rig and passing through said sleeve pipe into an ocean floor, said drill stem being spaced from said sleeve pipe to define an annular space therebetween;
   an end piece arrangement mounted on an end of said sleeve pipe and disposed in sealing relation with said drill stem for sealing said annular space, said end piece arrangement including a housing mounted on said sleeve pipe and a seal unit mounted on said drill stem and rotatably received in said housing;
   at least one exit passage in said sleeve pipe adjacent said end piece for passage of a flow of bore cuttings from said annular space; and
   a conduit system in communication with and extending from said exit passage for removal of the bore cuttings to a remote site.

* * * * *

UNITED STATES PATENT AND TRADEMARK OFFICE
CERTIFICATE OF CORRECTION

PATENT NO.    : 6,877,565 B2
DATED         : April 12, 2005
INVENTOR(S)   : Per Espen Edvardsen It is certified that error appears in the above-identified patent and that said Letters Patent is hereby corrected as shown below:

Column 7,
Line 9, "bare" should be -- bore --

Signed and Sealed this

Seventh Day of June, 2005

JON W. DUDAS
*Director of the United States Patent and Trademark Office*